(12) United States Patent
Mitelberg et al.

(10) Patent No.: US 8,540,735 B2
(45) Date of Patent: Sep. 24, 2013

(54) ENDOSCOPIC SUTURE CINCH SYSTEM

(75) Inventors: Vladimir Mitelberg, Austin, TX (US);
Donald K. Jones, Dripping Springs, TX (US)

(73) Assignee: Apollo Endosurgery, Inc., Austin, TX (US)

( * ) Notice: Subject to any disclaimer, the term of this patent is extended or adjusted under 35 U.S.C. 154(b) by 322 days.

(21) Appl. No.: 12/970,323

(22) Filed: Dec. 16, 2010

(65) Prior Publication Data

US 2012/0158023 A1    Jun. 21, 2012

(51) Int. Cl.
*A61B 17/04*    (2006.01)

(52) U.S. Cl.
USPC .............. 606/144; 606/148; 606/232

(58) Field of Classification Search
USPC ............. 606/139, 142, 144, 148, 151, 232
See application file for complete search history.

(56) References Cited

U.S. PATENT DOCUMENTS

| | | |
|---|---|---|
| 5,026,379 A | 6/1991 | Yoon |
| 5,041,129 A | 8/1991 | Hayhurst et al. |
| 5,141,520 A | 8/1992 | Goble et al. |
| 5,196,022 A | 3/1993 | Bilweis |
| 5,217,486 A | 6/1993 | Rice et al. |
| 5,304,185 A | 4/1994 | Taylor |
| 5,403,328 A | 4/1995 | Shallman |
| 5,433,725 A | 7/1995 | Christian et al. |
| 5,464,424 A | 11/1995 | O'Donnell, Jr. |
| 5,466,241 A | 11/1995 | Leroy et al. |
| 5,474,568 A | 12/1995 | Scott |
| 5,478,345 A | 12/1995 | Stone et al. |
| 5,514,159 A | 5/1996 | Matula et al. |
| 5,520,702 A | 5/1996 | Sauer et al. |
| 5,527,321 A | 6/1996 | Hinchliffe |
| 5,531,763 A | 7/1996 | Mastri et al. |
| 5,545,180 A | 8/1996 | Le et al. |
| 5,573,496 A | 11/1996 | McPherson et al. |
| 5,584,860 A | 12/1996 | Goble et al. |
| 5,584,861 A | 12/1996 | Swain et al. |
| 5,601,557 A | 2/1997 | Hayhurst |
| 5,626,590 A | 5/1997 | Wilk |
| 5,626,614 A | 5/1997 | Hart |
| 5,643,320 A | 7/1997 | Lower et al. |
| 5,649,940 A | 7/1997 | Hart et al. |
| 5,653,717 A | 8/1997 | Ko et al. |
| 5,662,658 A | 9/1997 | Wenstrom, Jr. |
| 5,669,917 A | 9/1997 | Sauer et al. |
| 5,681,331 A | 10/1997 | De la Torre et al. |
| 5,685,823 A | 11/1997 | Ito et al. |
| 5,690,655 A | 11/1997 | Hart et al. |
| 5,720,766 A | 2/1998 | Zang et al. |

(Continued)

*Primary Examiner* — Corrine M McDermott
*Assistant Examiner* — Alexander Orkin
(74) *Attorney, Agent, or Firm* — Gordon & Jacobson, PC

(57) ABSTRACT

A two-part suture cinch includes a collar and a plug. A cinch applicator is also provided, and includes an elongate tubular member, a plunger engaged within the distal end of the tubular member, a flexible shaft extending through the tubular member and plunger, and a proximal handle for moving the shaft longitudinally relative to the tubular member. The plunger includes a distal housing for the collar of the cinch, and the plug is coupled to the distal end of the flexible shaft. The suture is thread through the collar and a portion of the applicator. Operation of the applicator draws the plug into the collar and clamps the suture between the plug and collar. In addition, once the plug is coupled in to the collar, the plunger is displaced proximally to release the two-part cinch form the applicator. A method for applying the cinch is also provided.

32 Claims, 11 Drawing Sheets

(56) References Cited

U.S. PATENT DOCUMENTS

| | | |
|---|---|---|
| 5,782,862 A | 7/1998 | Bonutti |
| 5,814,071 A | 9/1998 | McDevitt et al. |
| 5,887,594 A | 3/1999 | LoCicero, III |
| 5,944,739 A | 8/1999 | Zlock et al. |
| 5,964,764 A | 10/1999 | West, Jr. et al. |
| 5,993,467 A | 11/1999 | Yoon |
| 6,010,525 A | 1/2000 | Bonutti et al. |
| 6,036,699 A | 3/2000 | Andreas et al. |
| 6,068,648 A | 5/2000 | Cole et al. |
| 6,086,600 A | 7/2000 | Kortenbach |
| 6,086,608 A | 7/2000 | Ek et al. |
| RE36,974 E | 11/2000 | Bonutti |
| 6,159,234 A | 12/2000 | Bonutti et al. |
| 6,171,316 B1 | 1/2001 | Kovac et al. |
| 6,200,329 B1 | 3/2001 | Fung et al. |
| 6,224,614 B1 | 5/2001 | Yoon |
| 6,293,961 B2 | 9/2001 | Schwartz et al. |
| 6,312,448 B1 | 11/2001 | Bonutti |
| 6,475,230 B1 | 11/2002 | Bonutti et al. |
| 6,635,073 B2 | 10/2003 | Bonutti |
| 6,656,182 B1 | 12/2003 | Hayhurst |
| 6,663,639 B1 | 12/2003 | Laufer et al. |
| 6,663,641 B1 | 12/2003 | Kovac et al. |
| 6,695,852 B2 | 2/2004 | Gleason |
| 6,699,183 B1 | 3/2004 | Wimmer |
| 6,719,763 B2 | 4/2004 | Chung et al. |
| 6,719,764 B1 | 4/2004 | Gellman et al. |
| 6,733,509 B2 | 5/2004 | Nobles et al. |
| 6,755,843 B2 | 6/2004 | Chung et al. |
| 6,808,491 B2 | 10/2004 | Kortenbach et al. |
| 6,866,673 B2 | 3/2005 | Oren et al. |
| 6,921,361 B2 | 7/2005 | Suzuki et al. |
| 6,955,643 B2 | 10/2005 | Gellman et al. |
| 7,033,379 B2 | 4/2006 | Peterson |
| 7,048,755 B2 | 5/2006 | Bonutti et al. |
| 7,083,630 B2 | 8/2006 | DeVries et al. |
| 7,083,638 B2 | 8/2006 | Foerster |
| 7,087,012 B2 | 8/2006 | Ishibiki |
| 7,090,690 B2 | 8/2006 | Foerster et al. |
| 7,094,246 B2 | 8/2006 | Anderson et al. |
| 7,147,652 B2 | 12/2006 | Bonutti et al. |
| 7,150,757 B2 | 12/2006 | Fallin et al. |
| 7,153,314 B2 | 12/2006 | Laufer et al. |
| 7,179,277 B2 | 2/2007 | Cunningham |
| 7,198,599 B2 | 4/2007 | Goto et al. |
| 7,204,802 B2 | 4/2007 | De Leval |
| 7,220,266 B2 | 5/2007 | Gambale |
| 7,235,086 B2 | 6/2007 | Sauer et al. |
| 7,264,624 B2 | 9/2007 | Nash et al. |
| 7,318,802 B2 | 1/2008 | Suzuki et al. |
| 7,371,215 B2 | 5/2008 | Colliou et al. |
| 7,530,985 B2 | 5/2009 | Takemoto et al. |
| 7,601,161 B1 | 10/2009 | Nobles et al. |
| 7,703,459 B2 | 4/2010 | Saadat et al. |
| 7,727,144 B2 | 6/2010 | Suzuki |
| 7,775,973 B2 | 8/2010 | Okada et al. |
| 7,776,066 B2 | 8/2010 | Onuki et al. |
| 7,785,348 B2 | 8/2010 | Kuhns et al. |
| 7,918,867 B2 | 4/2011 | Dana et al. |
| 7,931,661 B2 | 4/2011 | Saadat et al. |
| 7,935,128 B2 | 5/2011 | Rioux et al. |
| 7,988,656 B2 | 8/2011 | Uesugi et al. |
| 8,016,840 B2 | 9/2011 | Takemoto et al. |
| 8,021,376 B2 | 9/2011 | Takemoto et al. |
| 2003/0109891 A1* | 6/2003 | Dana et al. .................... 606/148 |
| 2005/0240199 A1 | 10/2005 | Martinek et al. |
| 2006/0259044 A1* | 11/2006 | Onuki et al. .................. 606/139 |
| 2007/0270907 A1* | 11/2007 | Stokes et al. ................. 606/232 |
| 2008/0234729 A1 | 9/2008 | Page et al. |
| 2009/0216308 A1 | 8/2009 | Hartley |
| 2009/0312775 A1 | 12/2009 | Gilkey et al. |

* cited by examiner

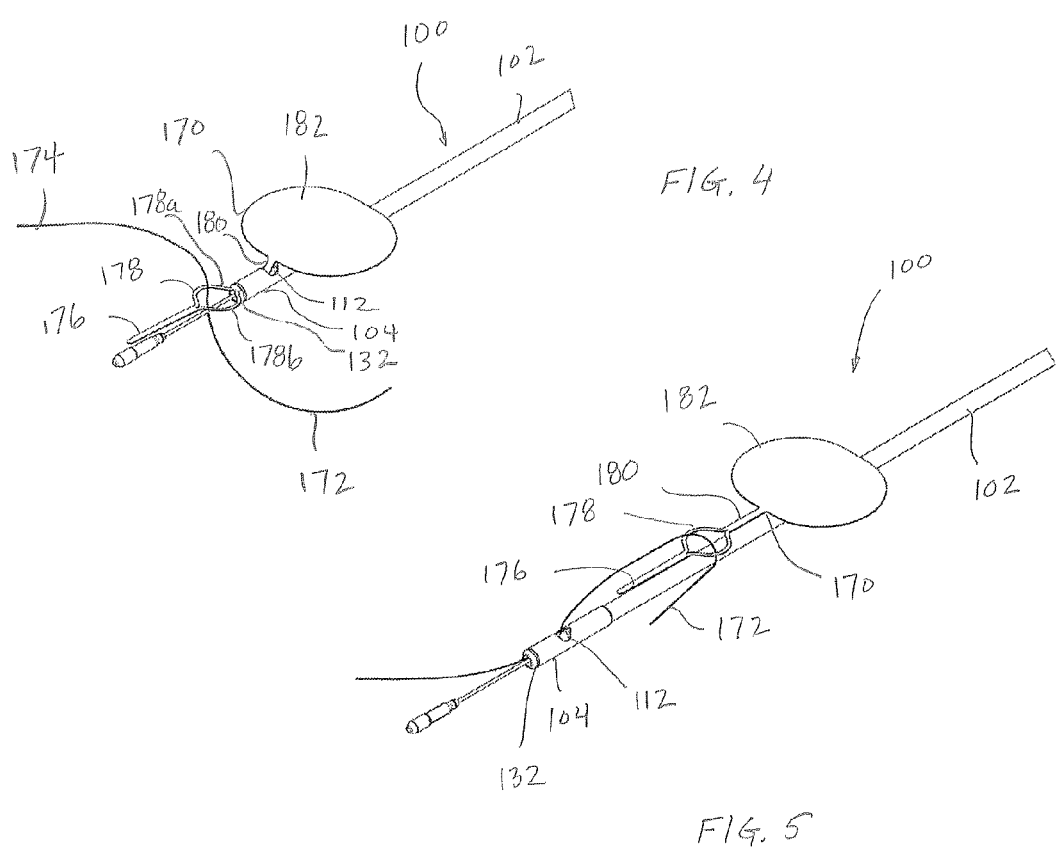

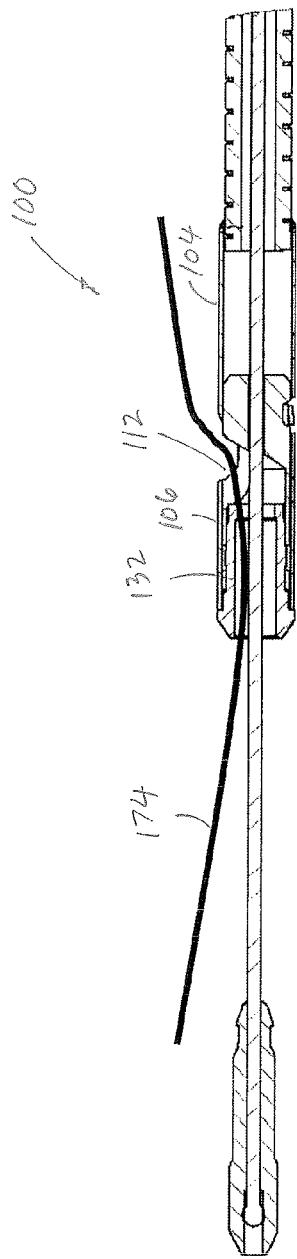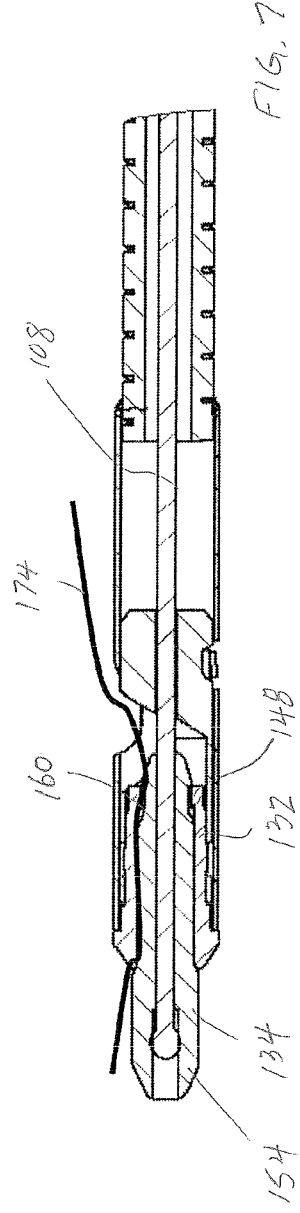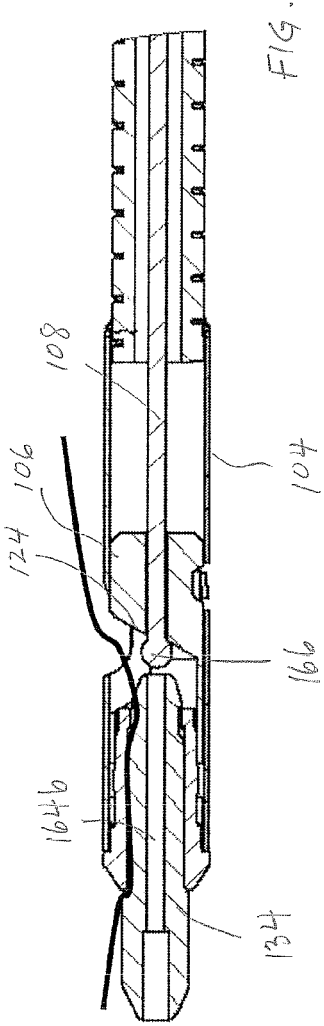

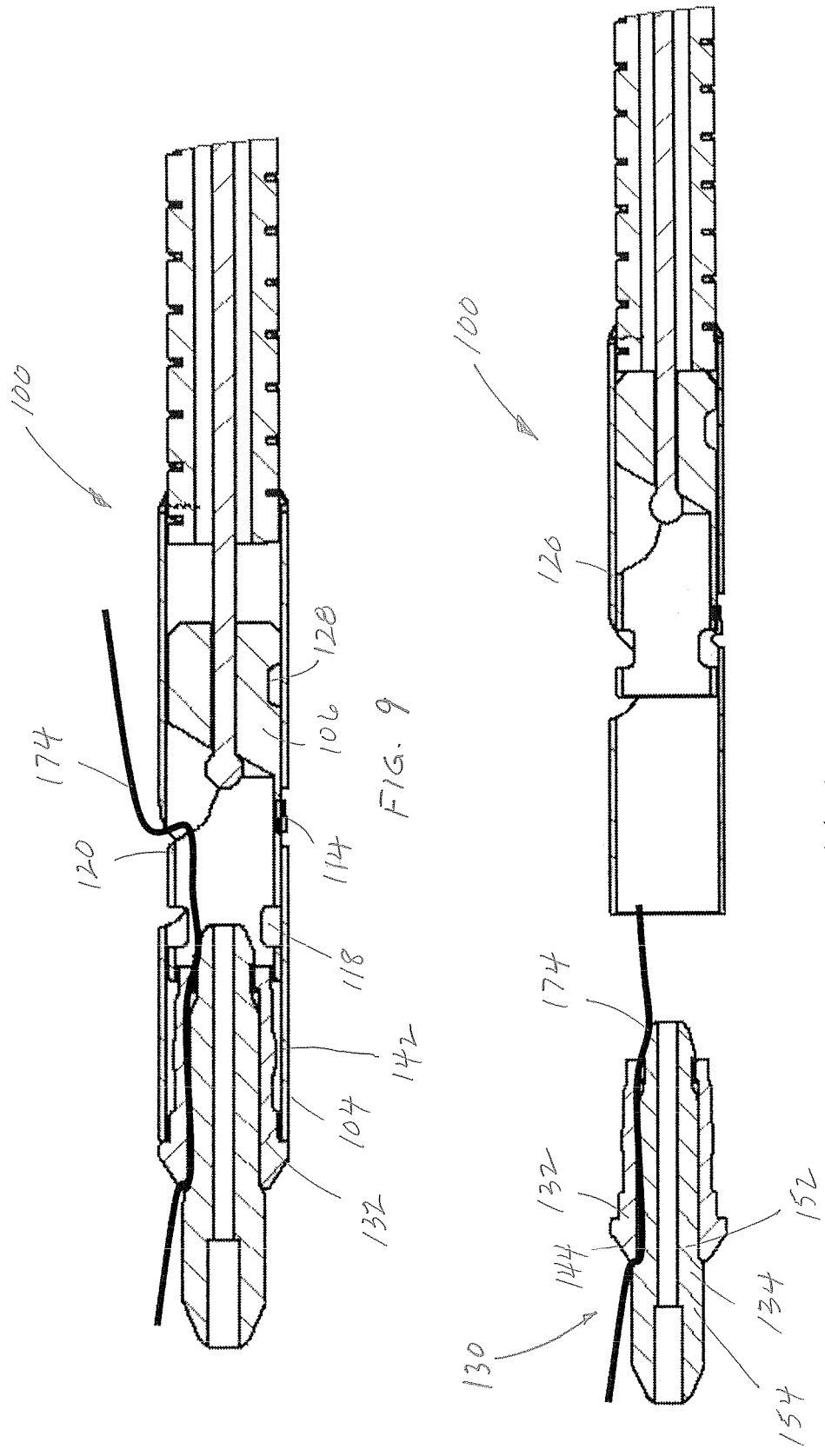

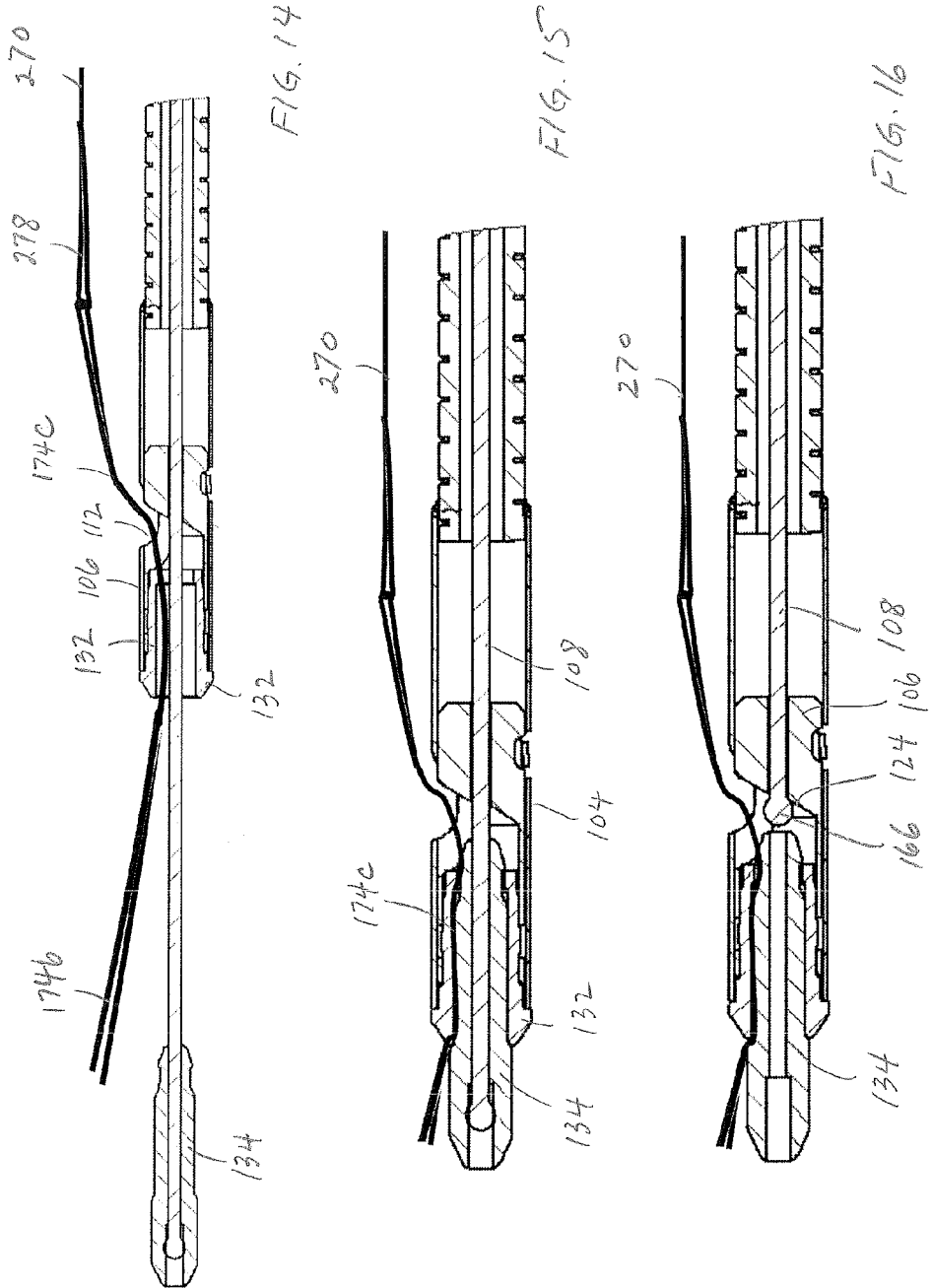

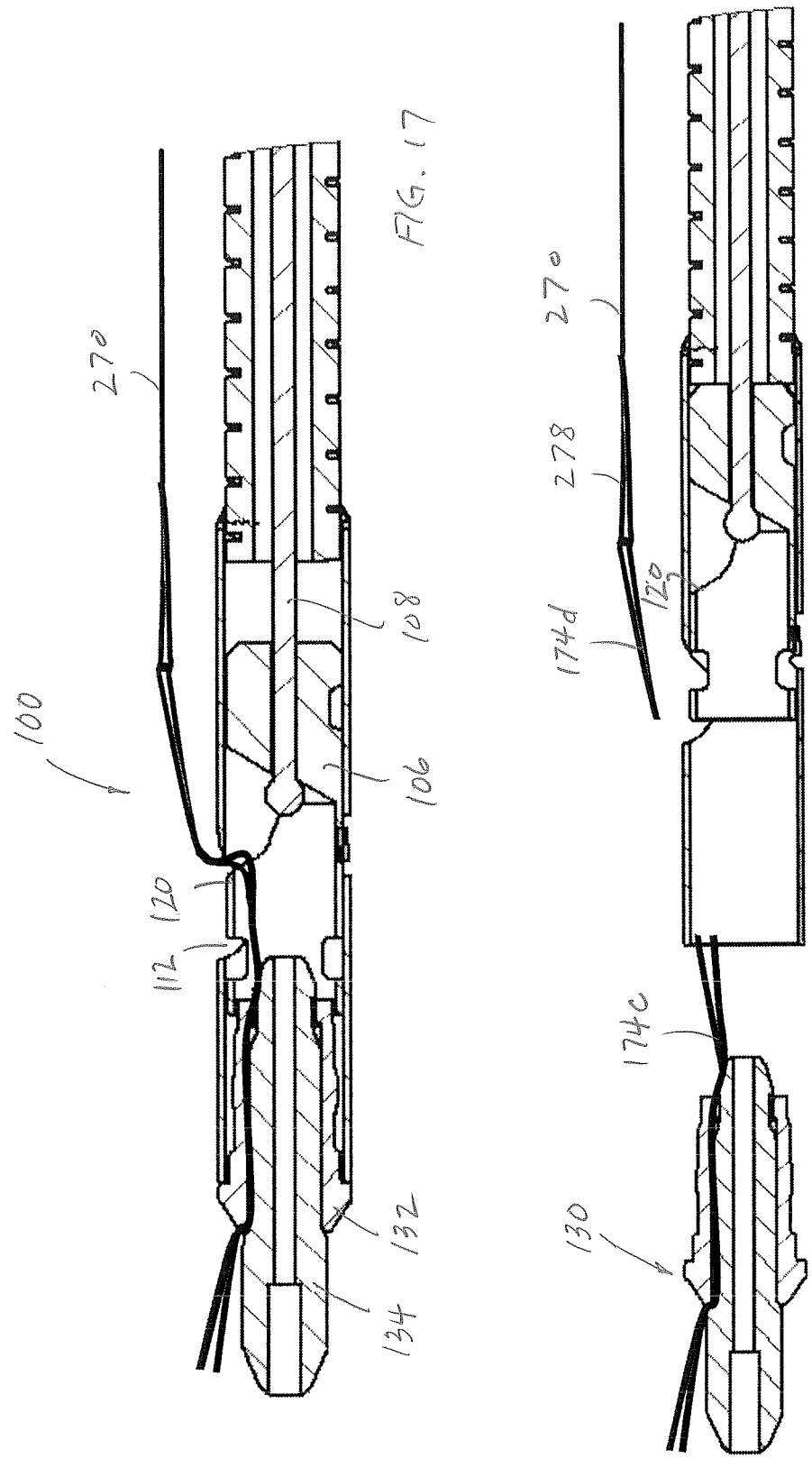

ENDOSCOPIC SUTURE CINCH SYSTEM

BACKGROUND OF THE INVENTION

1. Field of the Invention

The present invention relates to a device that can be inserted into a body through a natural orifice with an endoscope or other steerable guide member. The present invention may be used in conjunction with a suturing instrument to secure an applied suture to the tissue of a mammal, whether human or not, and whether or not alive.

2. State of the Art

Natural Orifice Translumenal Endoscopic Surgery (NOTES) involves passing surgical instruments in association with an endoscopic camera through a natural orifice, such as the mouth, vagina, or anus, to a desired organ. By avoiding major incisions through the skin, muscle, and nerves of the abdomen, patients may experience a quicker recovery with less pain and scarring while further reducing the post-operative risk of surgery.

In co-owned US Pub. No. 20090312775A1, an endoscopic suturing device suitable for use in a NOTES procedure is described. The device has a structure with a sufficiently small distal profile for delivery through a natural orifice, while providing a needle movable on an arm through a large opening and closing angle and which produces a large force upon the needle for piercing tissue to perform a surgical operation such as tissue approximation and suturing. A length of suture is permanently attached to the needle and forms stitches about tissue engaged at the distal end of the device as the needle is moved through the tissue and the distal end of the device is moved relative to the tissue. After one or more stitches have been formed in the tissue, the needle is released from the device and the free end of the suture is secured relative to the tissue. In accord with one manner of securing the free end of the suture, portions of the suture may be tied together about the tissue. In accord with another manner of securing the suture, a cinch element is advanced over the suture and cinches the tissue between the needle on one side of the tissue and the cinch on the other side of the tissue. The suture is then severed.

In addition to the cinch and cinch-applying instrument described in the above-referenced publication, other cinch instruments and deployable cinches are known. For example, referring to prior art FIG. 1, also known is a cinch applicator 10 for use in deploying the two parts 12, 14 of a cinch onto suture 16 in a NOTES procedure. The applicator 10 includes an elongate flexible tubular member 18, a hypotube 20 fixed to the distal end 22 of the flexible tubular member 18, a flexible shaft 24 extending through the tubular member 18 and the hypotube 20, and a proximal handle (not shown) for moving the shaft 24 longitudinally relative to the tubular member 18. The hypotube 20 defines a distal housing 26 and a proximal lateral window 28. A slidable plunger 30 provided with a guillotine 32 is provided within the hypotube 20, with the guillotine 32 fully proximal of the housing 26 and distal of the lateral window 28.

The two-part cinch includes a collar 12 and a plug 14 engageable within the collar. The collar 12 has a cylindrical outer shape that is retained in the distal housing 26 of the hypotube 20 with a simple dimpling mating structure. The collar 12 also includes a proximal inner lip 33, and an outer lip 34 seating at the distal end of the hypotube 20 and having a flat distal facing end 35. The plug 14 of the cinch is attached to the distal end of the flexible shaft 24. The plug 14 has an enlarged distal flange 36 corresponding in size and shape to the outer lip 34 on the collar 12. The plug 14 has an elongate tubular body 38 defining a throughbore 40 in which the flexible shaft 24 extends, and a proximal circumferential exterior groove 42. A distal portion of the shaft 24 has a bend 44 to facilitate retention within the throughbore 40. The distal end of the shaft 24 has a rounded bead 46 that sits at the flange 36 of the plug. The bend 44 and the bead 46 trap the flexible shaft relative to the plug.

In operation, from outside the patient, the proximal end of the suture 16 is thread through the collar 12 and hypotube 20 and out of the lateral window 28. Then the applicator 10 is advanced through an endoscope so that the elements of the cinch are provided adjacent the stitched tissue. When the handle is operated, the shaft 24 is retracted to draw the plug 14 into an interference fit within the collar 12, with the inner lip 33 of the collar positively engaging the outer groove 42 on the plug. The suture 16 is captured between the outer surface of the plug 14 and the inner surface of the collar 12 so that the cinch is secured to the suture. Upon further retraction of the shaft 24, the shaft is pulled such that the bend 44 and bead 46 of the shaft 24 are pulled all the way through the plug 14 until released therefrom, and drawn back into engagement with the plunger 30. As the shaft 24 is moved further proximally relative to the hypotube 20, movement of the shaft 24 causes the guillotine 32 to slide past the window 28 and sever the proximal portion of the suture 16 from the portion of the suture attached to the cinch. Once the suture 16 is severed, a jerking motion is applied to the applicator 10 to release the engagement formed by the dimpling structure between to the cinch 12, 14 and applicator 10.

The applicator and cinch are thereby together capable of effectively securing stitched suture to tissue.

SUMMARY OF THE INVENTION

Notwithstanding the effectiveness of the prior applicators and cinches, several improvements have been made which facilitate endoscopic application of a two-part cinch to suture. In accord with the invention, a system including a two-part suture cinch and cinch applicator is provided. The system has particular use in a NOTES procedure in which an endoscopic stitching instrument has applied one or more stitches of suture through tissue. In a mode of such stitching, a needle fixed to one of the suture is advanced through the tissue and carries the suture through the tissue. Once the tissue is sufficiently stitched to approximate the tissue, the system of the cinch and cinch applicator is provided for cinching the suture against the tissue and/or relative to the suture needle.

The cinch applicator includes an elongate tubular member, a plunger engaged within the distal end of the tubular member, a flexible shaft extending through the tubular member and plunger, and a proximal handle for moving the shaft longitudinally relative to the tubular member. The tubular member may be a unitary elongate construct or may be comprised of a proximal, longer, flexible, first tubular member and a distal, shorter, rigid, second tubular member, such as a hypotube, longitudinally coupled to the distal end of the first tubular member.

The tubular member includes a side window and a latch. The plunger includes an upper housing, a structure that engages the collar, a guillotine, a floor below the guillotine, and a base provided with a catch engaged by the latch of the tubular member to retain the position of the plunger within the tubular member. The suture cinch includes a collar and a plug. The collar is provided in the upper housing of the plunger and locked therein by an engagement at the plunger window. The distal end of the shaft extends beyond the distal end of the tubular member in an initial position with the plug coupled to the distal end of the flexible shaft. In operation the collar can be extended over the suture, and the flexible shaft can be withdrawn relative to the tubular member, drawing the plug into a coupled relationship with the collar and thereby clamping a portion of the suture between the plug and collar when the shaft is moved into the applied position. The coupled cinch plug and collar are released from engagement with the applicator and the suture is severed by movement of the guillotine past the side window of the tubular member.

In one embodiment, the cinch collar includes an elongate tubular body that is received in the housing of the plunger. The collar body includes a shallow partially circumferential rib that is engaged in a snap-fit engagement with structure of the plunger to lock the longitudinal location of the collar. When engaged, the collar body extends proximally beyond the guillotine of the plunger to shield the cutting edge of the guillotine. The collar has a distal outer lip that is received over the distal end of the tubular member and forms a distal taper that permits close approximation to tissue from various angles without damage to the tissue. The proximal end of the collar is stepped to a smaller diameter inner lip.

The cinch plug includes an elongate tubular body substantially longer in length than the collar. A central portion of the plug body substantially corresponds in length to the length of the collar, and has an outer diameter substantially corresponding to the inner diameter of the collar. A distal end portion of the plug is bulbous and has a larger diameter than the central portion. The plug body gradually increases in dimension from the central portion to define the bulbous distal end portion, which tapers to a distal tip. A proximal end portion gradually tapers away from the central portion to define a circumferential groove that corresponds in location with the step at the proximal end of the cinch collar when the collar and plug are mated are discussed below; the groove is substantially longer than the inner lip. There is no stepwise change in outer diameter along the central and distal portions of the plug; all diametrical changes are gradual. The proximal end tapers to a proximal tip that is provided with a small barb that can engage the proximal inner lip of the collar. A stepped throughbore is provided within the plug with the larger diameter of the throughbore located within the distal end portion. The flexible shaft is straight all the way through the plug body and includes an end with a bead that is retained in the larger diameter portion of the cinch plug throughbore (but too large to readily pass through the smaller diameter portion).

In operation, a free end of a length of suture attached to tissue must be loaded through the applicator. Such suture includes one end permanently fixed to the needle and located on one side of tissue, and a free end. In one embodiment, the free end of the suture extends through a working channel of an endoscope and out of the user-operated end of the endoscope. Loading the suture into the applicator requires advancing the suture through a pathway defined between the plug and the collar, through the collar and plunger, and out the window of the tubular member to back outside the applicator. The applicator is then advanced over the suture through the working channel of the endoscope to the tissue so that the cinch can be approximated with the tissue.

A suture threader may be provided to facilitate feeding the free end of suture through the pathway in the applicator. In one embodiment, the suture threader includes a distal guide, an intermediate resilient suture catch, a neck and a proximal handle. In an embodiment, a suture catch is defined by two arms attached at proximal and distal end and having central portions thereof biased away from one another. The threader is inserted through the pathway, in the opposite direction from which the suture must be inserted. That is, the guide is inserted from outside the applicator, through the window in the tubular member, through the collar and out the distal end of the collar. Once properly positioned, the catch is located distal of the collar and in an open position; i.e., with the central portion of the arms biased apart to a dimension larger than capable of passing through the collar, the neck extends within the portion of the pathway inside the applicator, and the handle is provided outside the applicator, preferably adjacent the window. The threader is dimensioned such that the open catch, neck, and handle are fixed in position relative to the applicator until forcibly withdrawn by the user. The applicator is preferably provided with the suture threader extending through the pathway in its as-assembled configuration by a manufacturer.

The suture is then inserted into the catch of suture threader, with a length of the suture drawn through the opening between the arms. Then the handle of the threader is pulled proximally to withdraw the threader from the pathway through the applicator, thus forcibly retracting the open arms against the collar and causing the arms to move against their bias into a closed position. In doing so, the arms also grasp the suture and draw the suture through the pathway defined by the collar, the plunger, and the window of the tubular member so that the applicator is situated about the suture ready for cinch application.

In another embodiment, the suture threader includes a proximal end extending out of the endoscope, a thin elongate portion extending alongside the cinch applicator within the working channel of the endoscope, and a distal portion being a U-shaped loop of suture. A portion of the threader is inserted through the pathway in the cinch applicator, with the U-shaped loop of suture extending between the cinch collar and cinch plug. An endoscopic stitching instrument is operated to move a suture attached to tissue through the U-shaped loop. The proximal end of the suture threader is actuated from outside the endoscope to retract the loop and cause the suture to be pulled through the pathway to the load the applicator with suture.

Once the applicator is loaded with suture, the distal end of the applicator is advanced along the suture until contacted at the location where the suture extends from the tissue. While the applicator is held at that location, tension is manually applied to the suture (from outside the proximal end of the endoscope), and the proximal handle is operated to move the flexible shaft from the initial position toward the applied position. As the shaft is moved proximally relative to the tubular member, the plug is drawn into the collar, capturing the suture between the exterior of the plug and the interior of the collar. The shape of the plug (relative to the prior art plug) prevents the shaft from prematurely detaching from the plug, which would potentially result in a misfire. In addition, the locked engagement between the collar and plunger prevents premature release of the collar from the applicator. As the plug is completely retracted into the collar, the barb at the proximal end portion of the plug engages the internal lip at the proximal end of the collar, thereby locking the plug to the collar with the suture trapped therebetween. Further retraction of the flexible shaft causes the bead at the distal end of the shaft to deform the smaller diameter portion of the throughbore of the plug and pull through the plug to be released from the plug. The bead is retracted against the floor of the plunger. Further force on the flexible shaft in the proximal direction results in (i) the engagement between the latch of the tubular member within the catch of the plunger to permit movement of the plunger within the tubular member, (ii) movement of the plunger relative to the tubular member such that the window of the plunger is retracted from over the rib of the collar, thereby unlocking the collar, freeing the cinch, and allowing the cinch to readily deploy from the applicator without any additional user activation, and (iii) movement of the guillotine into contact with the suture to sever the suture so that the cinched suture is freed from remaining suture extending through the working channel. With the suture cinched against the tissue, the applicator may then be withdrawn from the endoscope.

The placement of the plunger between the cinch collar and tubular member provides several advantages. First, a barrier is provided between the exterior surface of the collar and any sharp features of the tubular member. Second, the engagement features between the plunger and tubular member (catch and latch) offer precise component alignment. Third, the engagement features between the plunger and cinch collar (window and outer rib) offer precise location of the collar relative to the plunger. Fourth, because the collar extends back to hide the guillotine from the suture prior to disengagement of the latch and catch, the suture is protected from premature cutting. Fifth, the engagement features between the plunger and cinch prevent premature release of the collar until after the cinch has been applied.

In addition, the tapered and smoothly transitioning plug and tapered collar are easier to advance through the working channel on an endoscope. In addition, the longer plug length relative to the length of the collar provides a greater length over which the suture is captured. This provides enhanced retention strength. Moreover, the forward end of the suture will exit the cinch at the junction between the tapered distal lip of the collar and the transition between the central portion and the distal end portion of the plug. A large length of the cinch is provided to each side of the exit portion of the suture. As a result, the cinch may function as a T-tag, rotating from a longitudinal orientation (parallel to the longitudinal axis of the tubular member) to a transverse orientation to lie against the tissue thus providing a significantly larger contact surface area that provides greater resistance against tissue.

Additional objects and advantages of the invention will become apparent to those skilled in the art upon reference to the detailed description taken in conjunction with the provided figures.

BRIEF DESCRIPTION OF THE DRAWINGS

FIGS. 4 and 5 are perspective views showing use of a first embodiment of a suture threader to thread suture through a pathway of the cinch applicator according to the invention.

FIG. 6 is a longitudinal section view of the cinch applicator in a first position as loaded with suture by the first embodiment of a suture threader.

FIG. 7 is a longitudinal section view of the cinch applicator, as loaded with suture by the first embodiment of a suture threader, with the applicator in a second position in which the cinch plug has been drawn into the cinch collar to clamp suture between the plug and collar.

FIG. 8 is a longitudinal section view of the cinch applicator, as loaded with suture by the first embodiment of a suture threader, with the applicator in a third position in which the distal end of the shaft has been drawn through the cinch plug and against the floor of the plunger.

FIG. 9 is a longitudinal section view of the cinch applicator, as loaded with suture by the first embodiment of a suture threader, with the applicator in a fourth position in which the plunger has been retracted relative to the rigid, second tubular member of the cinch applicator.

FIG. 10 is a longitudinal section view of the cinch applicator, as loaded with suture by the first embodiment of a suture threader, with the applicator in a fifth position in which the plunger has been retracted to sever the suture and release the cinch.

FIG. 14 is a longitudinal section view of the cinch applicator in a first position being loaded with suture by the second embodiment of the suture threader.

FIG. 15 is a longitudinal section view of the cinch applicator, as loaded with suture by the second embodiment of a suture threader, with the applicator in a second position in which the cinch plug has been drawn into the cinch collar to clamp suture between the plug and collar.

FIG. 16 is a longitudinal section view of the cinch applicator, as loaded with suture by the second embodiment of a suture threader, with the applicator in a third position in which the distal end of the shaft has been drawn through the cinch plug and against the floor of the plunger.

FIG. 17 is a longitudinal section view of the cinch applicator, as loaded with suture by the second embodiment of a suture threader, with the applicator in a fourth position in which the plunger has been retracted relative to the rigid, second tubular member of the cinch applicator.

FIG. 18 is a longitudinal section view of the cinch applicator, as loaded with suture by the second embodiment of a suture threader, with the applicator in a fifth position in which the plunger has been retracted to sever the suture and release the cinch.

DETAILED DESCRIPTION OF THE PREFERRED EMBODIMENTS

A cinch applicator and two-part cinch are provided. The system has particular use in a NOTES procedure in which an endoscopic stitching instrument has applied one or more stitches of suture through tissue. However, it is appreciated that the system may have uses in other procedures, particularly other endoscopic procedures. The applicator and cinch may have uses in both open and closed surgical procedures, be used on humans as well as with other mammals, and may be used in procedures on living individuals as well as cadaverous bodies. The terms 'proximal' and 'distal' have their conventional meaning, with 'proximal' referring to a location relatively closer to a user-held and user-operated end of the cinch applicator, and 'distal' referring to a location relatively further from the user-held and user-operated end.

Figure 1:
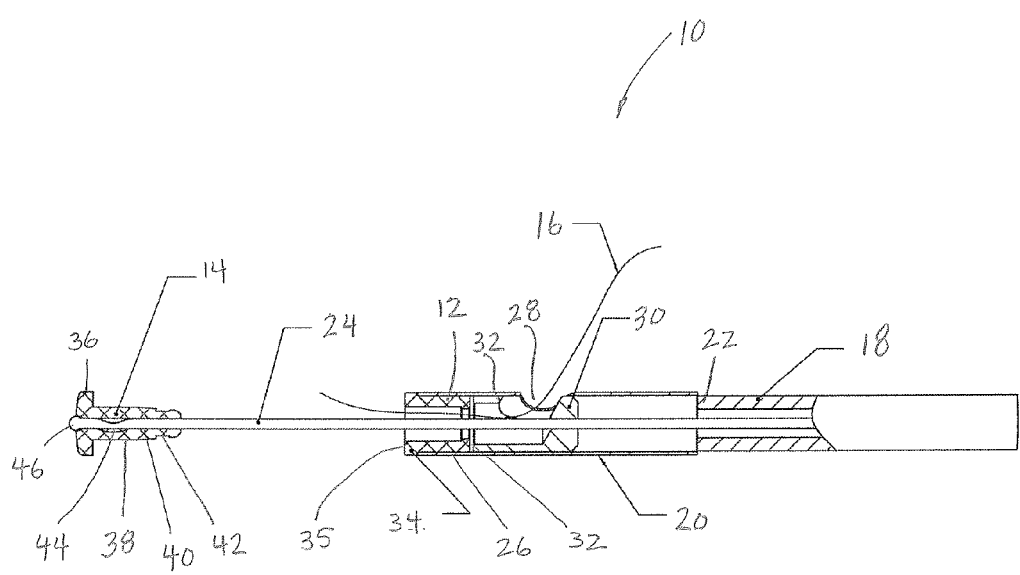
FIG. 1 is a partial section of a distal end of a prior art cinch applicator and a prior art two-part cinch.
Figure 2:
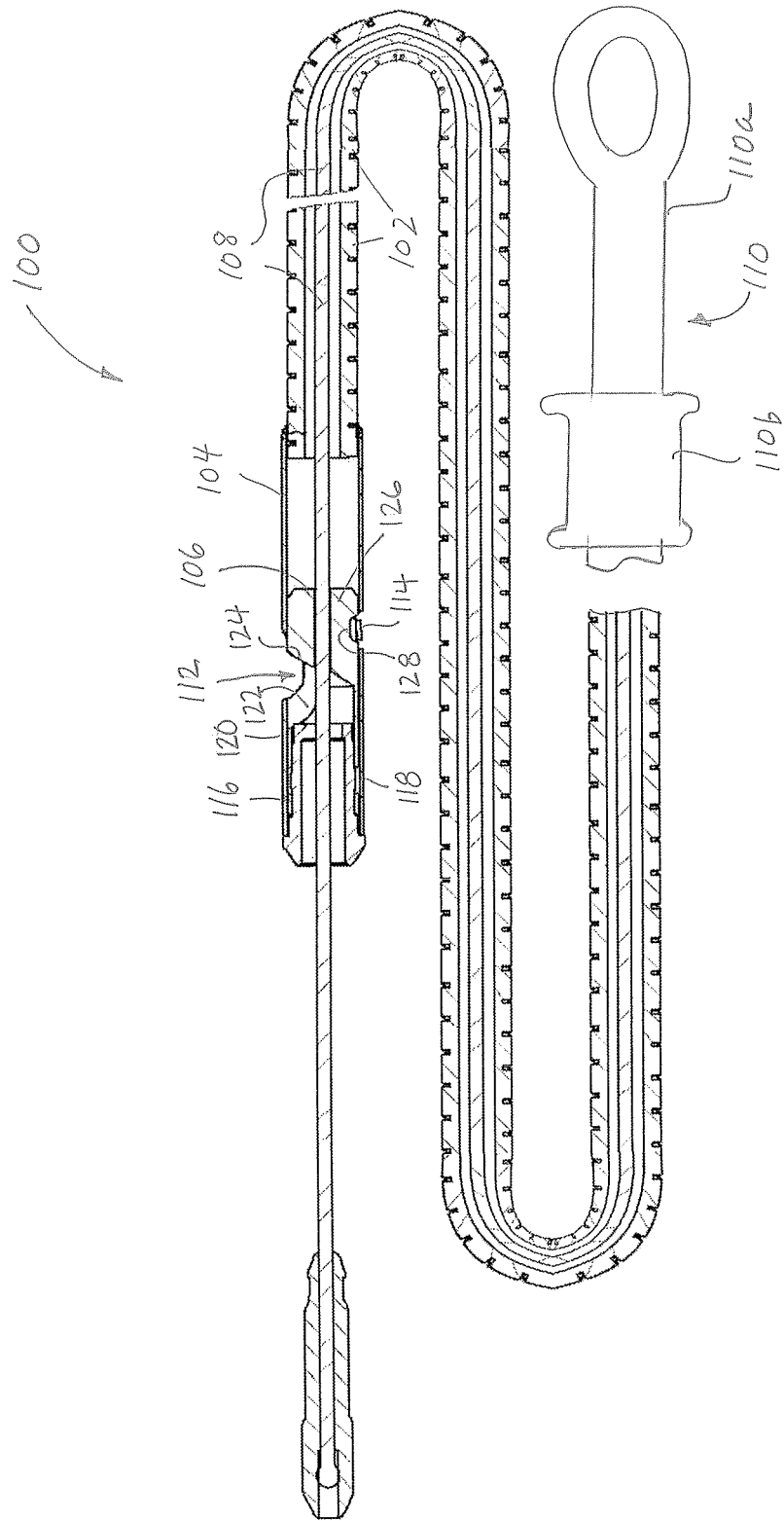
FIG. 2 is a partial section of a cinch applicator loaded with a two-part cinch according to an embodiment of the invention.

Referring now to FIG. 2, an embodiment of the cinch applicator 100 according to the invention includes an elongate, flexible, first tubular member 102, a shorter, rigid, second tubular member 104 fixed to the distal end of the flexible tubular member 102, a plunger 106 engaged within the second tubular member 104, a flexible shaft 108 extending through the flexible and rigid tubular members 102, 104 and plunger 106, and a proximal handle 110 for moving the flexible shaft 108 longitudinally relative to the tubular members 102, 104. The proximal handle 110 may include a stationary shaft 110a and movable slide or spool 110b conventionally used in association with many endoscopic instruments. Alternatively, the handle 110 may include a lever rotatable relative to a stationary member, or a movable trigger, or any other suitable handle assembly for longitudinally displacing the flexible shaft 108 relative to the first and second tubular members 102, 104. The flexible tubular member 102 may be made extruded from a polymer or be formed of a helically wound metal or polymer defining a structural coil, preferably provided with a lubricious sheath to facilitate its passage through a working channel of an endoscope. The rigid second tubular member 104 is preferably a section of a hypotube, although other constructs may be used, and may be crimped, bonded or otherwise attached at the distal end of the flexible first tubular member 102. The plunger 106 is preferably molded from plastic. The flexible shaft 108 is preferably a wire, cable, or other metal or polymeric filamentary structure capable of being subject to the tensile forces necessary to function in accord with the invention described below. That is, the shaft preferably is substantially inelastic and will not be deformed in elongation under the applied tensile forces. The flexible tubular member 102 and flexible shaft 108 have sufficient flexibility to be passed through a curvilinear working channel of an endoscope; even an endoscope that is retroflexed.

More particularly, the rigid second tubular member 104 preferably has a sufficiently short length that permits its passage through the non-linear working channel of an endoscope. By way of example, the length of the rigid tubular member 104 is preferably 12 mm. The rigid tubular member 104 includes a side window 112 and a latch 114. The latch 114 is preferably a leaf spring defined by a cut through a portion of the side wall of the rigid tubular member 104, the leaf spring extending into the interior of the tubular member and capable of being moved radially outward.

The plunger 106 includes an upper housing 116, a partially circumferential distal side opening 118, a guillotine 120 distally bordering a central opening 122 coinciding with the side window 112 of the rigid tubular member 104, a preferably sloped floor 124 proximally bordering the opening 122, and a base 126 provided with a catch 128. The catch 128 may comprise a groove, and is engaged by the latch 114 to retain the longitudinal position of the plunger 106 within the second tubular member 104. The latch 114 and catch 128 are respectively positioned to locate the plunger 106 within and relative to the second tubular member 104 at a specific location (and a reproducible location across the manufacture of many cinch applicators).

Figure 3:
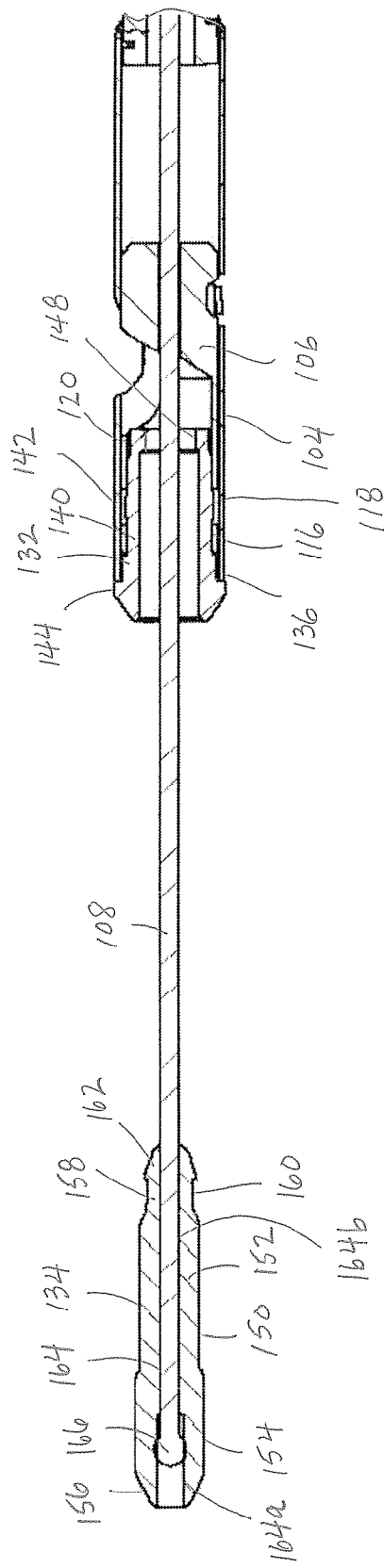
FIG. 3 is an enlarged distal end of view of the inch applicator and two-part cinch shown in FIG. 2.

Turning now to FIG. 3, the suture cinch includes two components—a collar 132 and a plug 134. Each of the collar 132 and plug 134 are preferably molded or machined from a biocompatible polymer. The collar 132 is provided in the upper housing 116 of the plunger 106 and is locked therein by an engagement between the collar and the plunger, described more particularly below. The distal end of the shaft 108 extends, in a first position, beyond the distal end 136 of the second tubular member 104, with the plug 134 coupled to the distal end of the flexible shaft 108.

More particularly, the cinch collar 132 includes an elongate tubular body 140 that is received in the housing 116 of the plunger 106. The collar body 140 is preferably approximately 4 mm in length. The body 140 includes a shallow partially circumferential rib 142 that is engaged in a snap-fit engagement into the side opening 118 of the plunger 106 to lock the collar to the plunger and relative to the second tubular member. When engaged, the collar body 140 extends proximally to shield the sharp edge of the guillotine 120 of the plunger 106 between the collar 132 and the second tubular member 104. The collar 132 has a distal lip 144 that is received over the distal end of the second tubular member 104 and forms a distal taper that permits close approximation to tissue from various angles without damage to the tissue. The proximal end of the collar 132 is stepped to a smaller diameter inner lip 148.

The cinch plug 134 includes an elongate tubular body 150 substantially longer in length than the collar 132. By way of example, the cinch plug 134 is preferably approximately 8 mm in length that, in view of how the cinch collar 132 and plug 134 are assembled as discussed below, is also the total cinch length. A central portion 152 of the plug body 150 substantially corresponds in length to the length of the collar 132, and has an outer diameter substantially corresponding to the inner diameter of the collar. A distal end portion 154 of the plug 134 is bulbous and has a larger diameter than the central portion 152. The body 150 gradually increases in dimension from the central portion 152 to define the bulbous distal end portion 154, which tapers to a distal tip 156. A proximal end portion 158 gradually tapers away from the central portion 152 to define a circumferential groove 160 that corresponds in location with the lip 148 at the proximal end of the cinch collar 132 when the collar and plug are mated are discussed below; the groove 160 is substantially longer than the step. There is no stepwise change in outer diameter along the central and distal portions 152, 154 of the plug. The proximal end portion 158 tapers to a proximal tip 162 which functions as a small barb that can engage the proximal inner lip 148 of the collar 132. A stepped throughbore 164 is provided through the plug 134, with the larger diameter portion 164a of the throughbore located within the distal end portion 154. The flexible shaft 108 is straight all the way through the plug body 134 and includes an end with a bead 166 that is provided in the larger diameter portion 164a of the throughbore 164 (but too large to readily pass through a smaller diameter portion 164b).

The cinch applicator may be provided with a suture threader to assist in feeding a free end of a length of suture stitched to tissue into the applicator. One embodiment of a suture threader 170 for manually feeding the free end 172 of a length of suture 174 stitched to tissue into the applicator 100 is shown in FIG. 4. Suture threader is ideally suited for threading a length of suture extending from the stitch, through a working channel of an endoscope and outside the patient suture, and then into the applicator. It is recognized that, according to a preferred use for the applicator and cinch, the opposite end of 175 the suture 174 is fixed to a needle 188 located on an opposite side of tissue 180 (See FIG. 11, discussed in more detail below). In one embodiment, the free end of the suture extends from the tissue and through the working channel to the user-operated end of an endoscope. Loading the free end 172 of suture into the cinch applicator 100 requires advancing the suture through a pathway defined between the collar 132 and plug 134, through the collar 132, and out through the window 112 of the rigid tubular member 104 to back outside the applicator. The applicator 110 is then advanced over the suture 174 through the working channel to the tissue so that the two-part cinch 130 can be approximated with the tissue.

The suture threader 170 includes a distal guide 176, an intermediate resilient suture catch 178, a neck 180, and a proximal handle 182. More specifically, the suture catch 178 is defined by two arms 178a, 178b attached at proximal and distal ends and having central portions thereof biased away from one another to form an eye therebetween that has a dimension larger than capable of passing through the collar 132. The arms are collapsed against their bias and forced through the pathway from a direction opposite from which the suture 174 is to be inserted. That is, the guide 176 is inserted from outside the applicator, through the window 112 of the second tubular member 102, and through the collar 132 and out the distal end of the collar. Once properly positioned, the suture catch 178 is located distal of the collar 132 and in an open position. The threader handle 182 is retained outside the applicator, preferably adjacent the window 112. The threader is dimensioned such that the handle 182 and open suture catch 178 are fixed in position relative to the applicator until forcibly withdrawn by the user. The applicator 100 is preferably provided with the suture threader 170 in position, in the as-manufactured condition as prepared for use by the user.

The free end 172 of the suture 174 is then thread into the eye defined by the open arms 178a, 178b of the installed suture catch 178. Referring to FIG. 5, then the threader handle 182 is pulled proximally to withdraw the threader 170 from the applicator 100, thus forcibly moving the arms 178a, 178b against their bias into a closed position, as retracted against the collar 132. Referring to FIGS. 5 and 6, the closed arms 178a, 178b grasp the free end 172 of suture 174 and draw the suture through the pathway defined through the collar 132, the plunger 106, and out of the window 112 of the second tubular member 104 so that the suture is thread through the applicator 100 for cinch application.

Once the suture 174 is thread through the described pathway of the cinch collar and cinch applicator (FIG. 6), the distal end of the cinch applicator is advanced over the suture 174. The suture 174 is pulled taut, and the distal end of the applicator is advanced along the suture until contacted against the location where the suture enters the tissue. While the applicator is held at that location, tension is manually applied to the suture (from outside the proximal end of the endoscope). Referring to FIG. 7, the proximal handle 110 of the applicator (FIG. 2) is then operated to move the flexible shaft 108 from the initial first position toward an applied position. As the shaft 108 is moved proximally relative to the second tubular member 104, the plug 134 is drawn into the collar 132, capturing the suture 174 between the exterior of the plug and the interior of the collar. The rounded bulbous shape of the plug 134 prevents the plug from inadvertently catching on tissue or another instrument that could cause premature detachment of the flexible shaft 108 from the plug 134, and potentially result in a misfire. Specifically, testing has shown that the reduced dimension and rounded shape of the distal end portion 154 of the plug (without a stepped expansion to a large flattened flange) significantly reduce misfiring associated with contact of the plug against approximated tissue relative to the prior art cinch. In addition, the locked engagement between the collar 132 and plunger 106 prevents premature release of the collar from the applicator. As the plug 134 is completely refracted into the collar 132, the barb 162 at the proximal end portion of the plug is captured by the internal step 148 at the proximal end of the collar 132, with the internal step seating in the groove 160, thereby locking the plug 132 to the collar 134 with the suture 174 trapped therebetween.

Referring to FIG. 8, further retraction of the flexible shaft 108 relative to the rigid tubular member 104 causes the bead 166 at the distal end of the shaft to slightly deform the smaller diameter portion 164b of the throughbore of the plug 134, and pull through the plug to be freed from the plug. The bead 166 is retracted against the floor 124 of the plunger 106.

Turning to FIGS. 9 and 10, further sufficient force on the flexible shaft 108 in the proximal direction results in (i) disengagement of the catch 128 of the plunger 106 from the latch 114 of the second tubular member 104 to permit movement of the plunger within the second tubular member, (ii) movement of the plunger 106 relative to the second tubular member 104 such that the window 118 of the plunger is retracted from over the rib 142 of the collar 132, thereby unlocking the collar 132 and freeing the engaged two-part cinch from the applicator, and readying the cinch to deploy from the applicator 100 without any additional user activation, and (iii) movement of the guillotine 120 into an exposed position into contact with the suture 174 to sever the suture so that the cinch is freed from remaining suture extending through the working channel. With the suture cinched against the tissue, the applicator 100 may then be withdrawn from the endoscope.

The use of the plunger 106 between the cinch collar 132 and second tubular member 104 provides several advantages. First, a barrier is provided between the exterior surface of the collar 134 and the sharp metal features of a metal hypotube (when such a structure is utilized for the second tubular member). Second, the engagement features between the second tubular member 104 and plunger 106 (latch 114 and catch 128) offers precise component alignment. Third, the engagement features between the plunger 106 and cinch collar 132 offer precise location of the collar relative to the plunger. This is important, as the collar can be precisely positioned to extend back to hide the guillotine 120 from the suture 174 prior to intentional cutting, thereby protecting the suture from premature cutting. Fourth, the engagement features between the plunger 106 and cinch collar 132 prevent premature release of the cinch (or just) collar until after the cinch has been intentionally applied.

Figure 11:
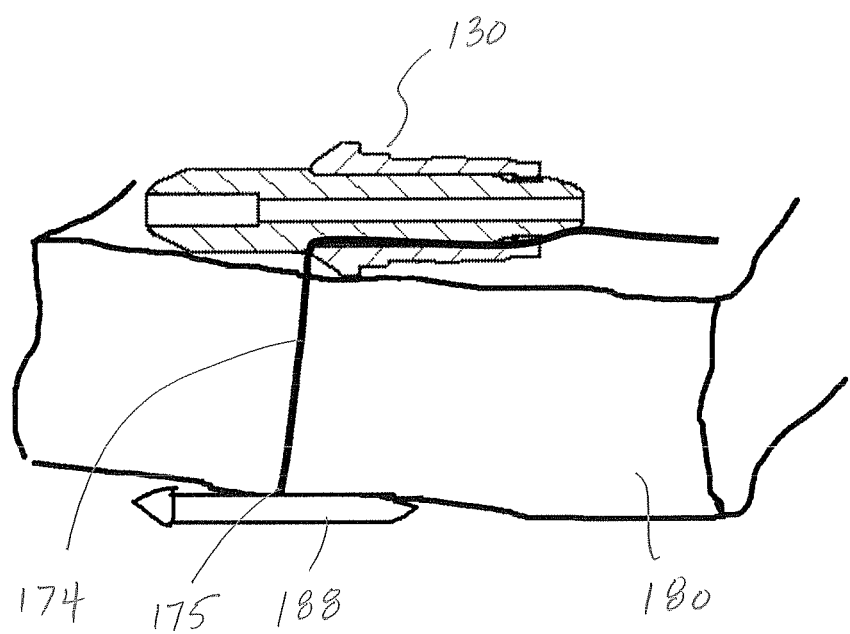
FIG. 11 is a perspective partial section view of tissue with a cinched suture on one side of the tissue and a needle on the other side of the tissue.

It is appreciated that the taper-transitioning plug 134 and tapered collar 132 are easier to advance through the working channel on an endoscope; i.e., the shapes of such components specifically overcome prior art issues with respect to feeding the structure of components through a working channel. In addition, the longer length of the plug 134 relative to the length of the collar 132 provides a greater length over which the suture is captured. This provides enhanced retention strength. Moreover, referring back to FIG. 10, the forward end of the cinched suture will exit the cinch at the junction between the tapered distal lip 144 of the collar 132 and the transition between the central portion 152 and the distal end portion 154 of the plug 134. A large length of the cinch 130 is provided to each side of the exiting suture. Referring to FIG. 11, as a result, the coupled cinch 130 may function as a T-tag, rotating from a longitudinal orientation (parallel to the longitudinal axis of the second tubular member) to a transverse orientation to lie against the tissue 186, thus providing a significantly larger contact surface area that provides greater resistance against tissue and thereby prevent pull-through. FIG. 11 also show a needle 188 attached to the suture on the side of tissue opposite the cinch 130.

Figure 12:
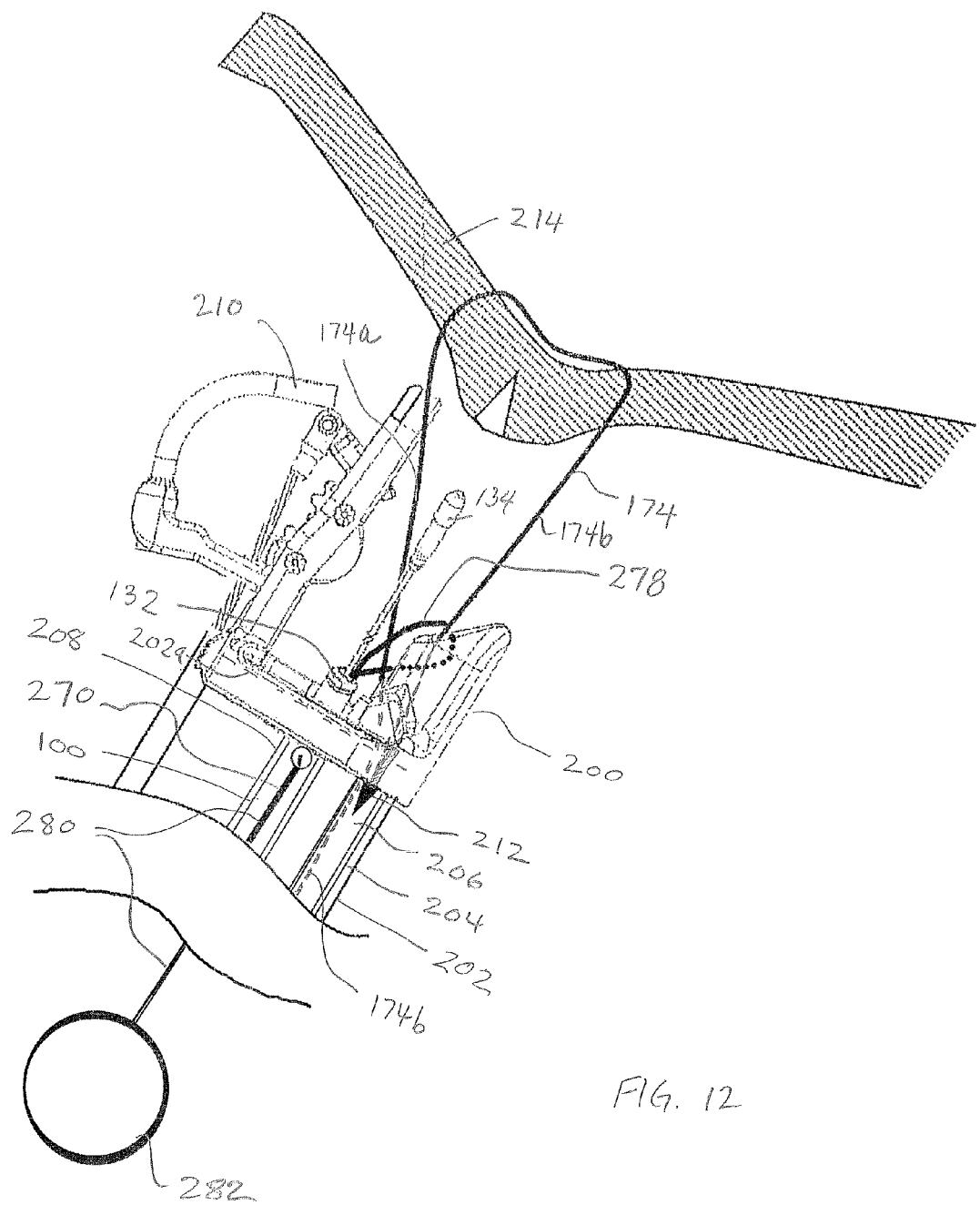
FIGS. 12 and 13 illustrate use of a second embodiment of a suture threader in conjunction with an endoscope and endoscope suture stitching device to thread suture through a pathway of the cinch applicator according to the invention.

It is also appreciated that the suture can be thread through the pathway while the applicator is in situ, i.e., with the applicator extended through the working channel of the endoscope and the applicator located adjacent the stitch. Turning now to FIG. 12, an endoscopic stitching instrument 200 is shown mounted at the distal end of an endoscope 202. The endoscope includes a first working channel 204 through which a needle catch device 206 extends and a second working channel 208 through which the cinch applicator 100 extends. The stitching instrument 200 includes an arm 210 that rotates a releasable needle 212 in an arc through captured tissue 214 and into engagement with the needle catch device 206 (the needle shown released from the arm and engaged in the catch device). A first portion 174a of the suture extends within the first working channel 204 along the outside of the catch device 206, and a second portion 174b of the suture extends between the tissue 214 and the needle 212. The needle 212 can be selectively engaged to the needle catch device 206 and released from the arm 210 for repositioning of the arm relative to the needle 212 and tissue 214 to advance a stitch of suture 174. Use of the endoscopic stitching instrument 200 is described in more detail in co-owned US Pub. No. 20090312775A1. Once the desired stitch is complete, the cinch applicator 100 is advanced through the second working channel 208.

The cinch applicator 100 is provided with another embodiment of a suture threader 270. The suture threader 270 includes a distal loop 278, a central portion 280 and a proximal end 282. The distal loop 278 has an opening of sufficient size to receive the needle 212 and as well the second portion 174b of the needle suture 174 therethrough (with the first portion 174a residing outside the loop 278). When the cinch applicator 100 is fully advanced into the working channel 208, the loop 278 is naturally positioned to receive the needle 212 within the loop 278 as the arm 210 is rotated to advance the needle into the needle catch device 206. The distal loop 278 is also sufficiently small to be able to be drawn back through the pathway (defined through the collar 132, the plunger 106, and the window 112 of the second tubular member 104 (see FIG. 14)) in conjunction with the second portion 174b of the needle suture 174. The distal end 278 may comprises a structure other than a loop, such as J-shaped construct or another suitable shape for receiving and retaining the second portion 174b of the needle suture as it is pulled back through the pathway, and may be made from a material other than suture. The central portion 280 of the threader 270 is preferably a elongate flexible element, preferably a strand of suture, extending from the loop 278. At least one of the distal and central portions 278, 280 extends through the pathway defined through the collar 132, the plunger 106, and out of the window 112 of the second tubular member 104, with the central portion 280 extending alongside the full length of the applicator 100, while the applicator is inserted within the working channel 208 of the endoscope (i.e., in a position with the cinch plug 134 extending out of the distal end of the endoscope 202, and the cinch collar 132 located even with or distal the distal face 202a of the endoscope). The proximal end of the suture threader 282 extends out of the proximal end of the second working channel 208 and is accessible to a user of the endoscope to permit manual retraction of the suture threader 270 relative to the cinch collar 132. The proximal end 282 may include a further extension of the suture comprising the central portion 280, or may be in the form of a finger loop (as shown), a dedicated handle, or some integration into the handle 110 (FIG. 2) that operates movement of the cinch plug 134 relative to the cinch collar 132. Once the stitching instrument 200 has been operated to move the needle 212 through the loop 278 at the distal end of the threader, a consequence is that the second portion 174b of the suture has also been thread through the loop 278 (with the portion 174a located outside the loop).

Figure 13:
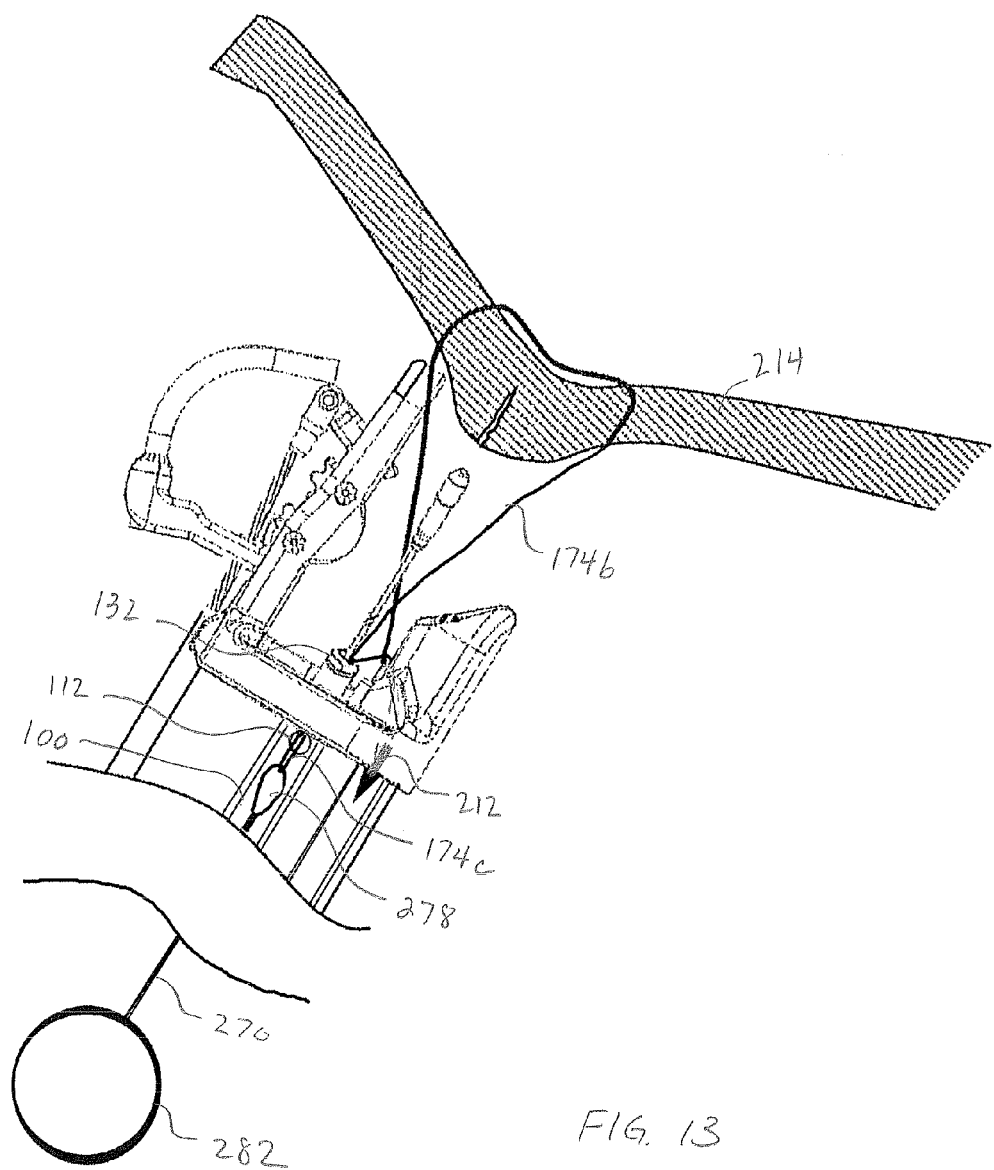

Referring to FIGS. 13 and 14, once the second portion 174b of the suture is situated within the loop 278, the proximal end 282 of the suture threader 270 is manipulated to retract the loop 278 and pull a captured portion of the distal portion 174a of the suture toward the collar 132. As the suture portion 174b is pulled in this manner (noting that the suture portion 174b is coupled to both the tissue 214 and the needle), the retracted suture portion 174b is doubled-over (at 174c) and pulled into and through the pathway (132, 106, 112) and out of the side window 112 in this doubled-over configuration. The distal loop 278 may be self-closing as it is pulled (like a noose) to assist in retaining a grip on the suture portion 174b as its pulled through the pathway (and later cut as described hereinafter). The suture threader is retracted until the suture is drawn through the side window 112. At this point, the distal end loop 278 of the suture threader resides outside the applicator 100 and within the second working channel 208.

With the suture portion 174b thread through the pathway of the applicator 100, the applicator is operated as described above to secure the cinch onto the suture. Briefly, with reference to FIG. 15, the distal end of the collar 132 is advanced to the tissue 214, and cinch wire 108 is moved relative to the hypotube 104 to cause the collar 132 to draw the plug 134 into the collar 132, thereby capturing the doubled-over portion 274c of suture between the plug and collar. It is appreciated that the collar 132 and plug 134 are appropriately dimensioned and of a material that accommodates the thickness of the doubled-over suture portion 274c. Then, referring to FIG. 16, the cinch wire 108 is retracted relative to the plug 134 to release the bead 166 at the distal end of the wire from the plug 134 and draw the bead 166 against the floor 124 of the plunger 106. Referring to FIG. 17, as the plunger 106 is fully retracted, the cinch 130 is released from mechanical engagement with the applicator 100. In addition, the guillotine 120 of the plunger 106 begins to move across the window 112. Further retraction of the plunger 106, as shown in FIG. 18, causes the guillotine 120 to be drawn across the doubled-over suture 174c and sever it, leaving a remaining portion 174d coupled to the loop 278 of the suture threader 270. Once the suture is severed, the suture threader 270 may be withdrawn from the endoscope working channel. The applied cinch 130 has the same advantages described above.

There have been described and illustrated herein embodiments of a cinch applicator and a method of applying a cinch. While particular embodiments of the invention have been described, it is not intended that the invention be limited thereto, as it is intended that the invention be as broad in scope as the art will allow and that the specification be read likewise. Thus, while particular dimensions have been described for portions of the cinch applicator, it will be appreciated that other suitable dimensions for components can be used as well. In addition, while preferred dimensions are presented for the two-part cinch, it is appreciated that the collar and plug may be provided in different dimensions as well. Also, while preferred materials are described, it is appreciated that other materials can be used. It will therefore be appreciated by those skilled in the art that yet other modifications could be made to the provided invention without deviating from its scope as claimed.

What is claimed is:

1. A cinch applicator for applying a suture cinch to suture, comprising:
   a) an elongate flexible first tubular member having proximal and distal ends;
   b) a relatively rigid second tubular member having proximal and distal ends, said proximal end of said second tubular member fixed to said distal end of said flexible first tubular member, said second tubular member defining a side window and defining a latch;
   c) a plunger situated within said second tubular member, said plunger having an upper housing for receiving at least a portion of the cinch, a guillotine provided with a cutting edge located distally relative to said side window of said second tubular member and retractable past said side window of said second tubular member when said plunger is moved proximally relative to said second tubular member, a floor proximal to said guillotine, and a catch engaged by said latch to retain a longitudinal position of said plunger within said second tubular member;

d) a flexible shaft having proximal and distal ends; and e) a proximal handle coupled to said proximal ends of said first tubular member and said flexible shaft to move said distal end of said flexible shaft relative to said distal end of said second tubular member.

2. A cinch applicator according to claim 1, wherein each of said first tubular member and said shaft have sufficient flexibility to extend through a working channel of an endoscope flexed through a non-linear pathway.

3. A cinch applicator according to claim 2, wherein said second tubular member is a portion of a metal hypotube.

4. A cinch applicator according to claim 2, wherein said first tubular member comprises a wound coil.

5. A cinch applicator according to claim 1, wherein said latch is a leaf spring.

6. A cinch applicator according to claim 1, wherein said flexible shaft defines a bead at its distal end.

7. A cinch applicator according to claim 1, wherein said proximal handle is operable to cause said distal end of said flexible shaft to be in,
a first position in which said distal end of said flexible shaft is in a longitudinally advanced location relative to said distal end of said second tubular member,
a second position in which said distal end of said flexible shaft is retracted relative to said first position,
a third position in which said distal end of said flexible shaft is contacted against said floor of said plunger, and
a fourth position in which said distal end of said flexible shaft has applied a sufficient proximal force against said plunger to overcome said latch so that said plunger is retracted to effect movement of said cutting edge at least partially past said side window of said second tubular member.

8. A cinch applicator according to claim 1, further comprising a cinch collar for attachment to suture, said cinch collar positioned within said housing of said plunger, said cinch collar having an external protuberance, said plunger defining a partially circumferential window, and said protuberance engaging within said window to lock said collar within said plunger.

9. A cinch applicator according to claim 1, further comprising:
a cinch collar provided in said housing of said plunger; and
a cinch plug attached to said distal end of said flexible shaft,
wherein said handle is operable to retract said flexible shaft such that said cinch plug is drawn back into a coupled engagement with said cinch collar.

10. A cinch applicator according to claim 9, wherein said cinch collar has an external protuberance, said plunger defines a partially circumferential window, and said protuberance engages within said window to lock said collar within said plunger.

11. A cinch applicator according to claim 9, further comprising a length of suture, said suture extending through said cinch collar and out of said side window.

12. A cinch applicator according to claim 9, wherein said collar includes a proximal end that shields said cutting edge from said suture.

13. A cinch applicator according to claim 12, wherein when said plunger is retracted, said cutting edge is exposed to said suture.

14. A cinch applicator according to claim 1, further comprising a cinch including a collar and a plug, said collar engaged within said housing of said plunger, and
collar upon longitudinal displacement of said flexible shaft.

15. A cinch applicator according to claim 14, further comprising a suture threader for retracting the suture from external said applicator proximally through said collar into said plunger and laterally out of said side window.

16. A cinch applicator according to claim 15, wherein said suture threader is actuatable to move said suture from external said applicator proximally through said collar into said plunger and laterally out of said side window when said cinch applicator is located within a working channel of an endoscope.

17. A cinch applicator according to claim 16, wherein said suture threader comprises a distal end having a loop and a flexible longitudinal central portion.

18. A cinch applicator according to claim 15, wherein said suture threader includes an elongate distal guide, a suture catch defining an eye, a proximal threader handle, and a neck joining said suture catch and said threader handle,
wherein said suture catch extends at least partially beyond said distal end of said second tubular member, said threader handle is located outside said first and second tubular members, and said neck extends within said second tubular member, and said suture catch compressible to be withdrawn through said distal end and side window of said second tubular member when a suitable force is applied to said threader handle.

19. A cinch applicator according to claim 18, wherein said suture catch of said suture threader includes first and second resilient arms biased apart from one another to define said eye therebetween.

20. A cinch applicator according to claim 18, wherein:
said suture threader is of a generally flat construct.

21. A cinch applicator according to claim 15, wherein:
said suture threader is of a generally flat construct.

22. A cinch applicator for applying a suture cinch to suture, comprising:
a) an elongate tubular member having proximal and distal ends, said distal end including a side window and a first engagement member;
b) a plunger situated within said tubular member, said plunger having a distal housing, a proximal floor, and a second engagement member engaged by said first engagement member to retain a longitudinal position of said plunger within said tubular member;
c) a shaft having proximal and distal ends; and
d) a proximal handle for moving said flexible shaft longitudinally relative to said tubular member from,
a first position in which said distal end of said flexible shaft is located distal of said floor of said plunger,
a second position in which said distal end of said flexible shaft is moved into contact against said floor of said plunger, and
a third position in which said first and second engagement members are disengaged and said plunger is moved proximally relative to said tubular member.

23. A cinch applicator according to claim 22, further comprising:
a releasable cinch collar engaged within said housing of said plunger, wherein in said third position said housing is retracted from over said cinch collar to release said collar from said housing.

24. A cinch applicator according to claim 23, wherein said plunger includes a cutting edge and in said first and second positions said cinch collar extends proximally beyond said cutting edge to shield said cutting edge.

25. A cinch applicator according to claim 24, wherein in said third position said plunger is retracted relative to said cinch collar to expose said cutting edge.

26. A cinch applicator according to claim 24, wherein said plunger is provided radially between said cinch collar and said tubular member.

27. A cinch applicator according to claim 23, further comprising:
   a plug for axially mating with said cinch collar, said plug releasably coupled to said distal end of said flexible shaft.

28. A cinch applicator according to claim 22, wherein said plunger includes a cutting edge, and in said third position said cutting edge is moved across at least a portion of said side window.

29. A cinch applicator according to claim 28, wherein in said third position said cutting edge is moved across said entire side window.

30. A cinch applicator according to claim 22, wherein said plunger is close fitting within said tubular member.

31. A cinch applicator according to claim 22, wherein said tubular member comprises a proximal, flexible first tubular member and a distal, rigid, second tubular member.

32. A cinch applicator according to claim 22, said tubular member includes at least a first portion that is flexible, and each of said first portion and said shaft have sufficient flexibility to extend through a working channel of an endoscope flexed through a non-linear pathway.

\* \* \* \* \*